(12) United States Patent
Nagel et al.

(10) Patent No.: US 10,174,751 B2
(45) Date of Patent: Jan. 8, 2019

(54) PUMP CHAMBER FOR A PERISTALTIC PUMP

(75) Inventors: Thomas Nagel, Tharandt (DE); Rene Richter, Tharandt (DE); Robert Witt, Dresden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 886 days.

(21) Appl. No.: 13/383,974

(22) PCT Filed: Jul. 14, 2010

(86) PCT No.: PCT/EP2010/060123
§ 371 (c)(1),
(2), (4) Date: Apr. 17, 2012

(87) PCT Pub. No.: WO2011/006921
PCT Pub. Date: Jan. 20, 2011

(65) Prior Publication Data
US 2012/0189476 A1    Jul. 26, 2012

(30) Foreign Application Priority Data

Jul. 14, 2009   (EP) .................................... 09009186

(51) Int. Cl.
*F04B 43/14*   (2006.01)
*F04B 43/00*   (2006.01)
(Continued)

(52) U.S. Cl.
CPC .......... *F04B 43/14* (2013.01); *F04B 43/0072* (2013.01); *F04B 43/1253* (2013.01);
(Continued)

(58) Field of Classification Search
CPC .... F04B 43/14; F04B 43/0072; F04B 43/123; F04B 43/1253; F04B 23/028; A61M 2205/12; A61M 5/14232
(Continued)

(56) References Cited

U.S. PATENT DOCUMENTS

| 40,195 A | * | 10/1863 | Smith ...................... F03B 7/00 |
| | | | 417/477.12 |
| 533,575 A | | 2/1895 | Wilkens |

(Continued)

FOREIGN PATENT DOCUMENTS

| DE | 19745999 A1 | 4/1999 |
| DE | 102006047613 A1 | 4/2008 |

(Continued)

*Primary Examiner* — Peter J Bertheaud
(74) *Attorney, Agent, or Firm* — McCarter & English, LLP

(57) ABSTRACT

The invention relates to a pump chamber (1) for a peristaltic pump, the pump chamber (1) comprising an elongate cavity (1.1) defined between an elastically deformable chamber wall (1.2) and a rigid chamber (1.3) wall, wherein the elastically deformable wall (1.2) and the rigid wall (1.3) are arranged as a one-piece part by two-component injection molding. The invention also refers to a method for producing the pump chamber (1) for a peristaltic pump, the method comprising a two-component injection molding of the elastically deformable wall (1.2) and the rigid chamber wall (1.3) thereby forming them as a one-piece part.

19 Claims, 3 Drawing Sheets

Figure 1:
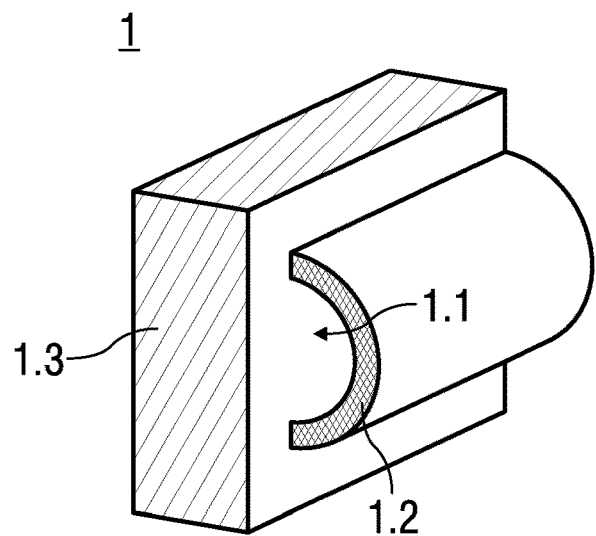

(51) Int. Cl.
*F04B 43/12* (2006.01)
*A61M 5/315* (2006.01)
*A61M 5/142* (2006.01)
*A61M 5/20* (2006.01)
*A61M 5/30* (2006.01)

(52) U.S. Cl.
CPC ..... *A61M 5/14232* (2013.01); *A61M 5/14244* (2013.01); *A61M 5/20* (2013.01); *A61M 5/30* (2013.01); *A61M 5/31525* (2013.01); *A61M 5/31546* (2013.01); *A61M 2205/12* (2013.01); *F04B 43/123* (2013.01); *F04B 43/1284* (2013.01); *Y10T 29/49236* (2015.01)

(58) Field of Classification Search
USPC .............................. 417/477.2, 477.9, 477.12
See application file for complete search history.

(56) References Cited

U.S. PATENT DOCUMENTS

| | | | | |
|---|---|---|---|---|
| 910,125 | A * | 1/1909 | Graser | F04B 43/0072 417/477.12 |
| 2,519,642 | A * | 8/1950 | Ford | F04B 43/14 417/477.12 |
| 2,885,966 | A * | 5/1959 | Ford | 417/477.7 |
| 3,039,442 | A * | 6/1962 | Hornschuch | F03C 7/00 417/475 |
| 3,507,585 | A * | 4/1970 | Mercer | F04B 43/0054 417/475 |
| 4,332,534 | A * | 6/1982 | Becker | F04B 43/0054 418/153 |
| 4,392,794 | A * | 7/1983 | Foxcroft | F04B 43/1269 417/475 |
| 4,545,745 | A * | 10/1985 | Barreca | F04B 43/14 417/477.12 |
| 5,226,895 | A | 7/1993 | Harris | |
| 5,279,586 | A | 1/1994 | Balkwill | |
| 5,304,152 | A | 4/1994 | Sams | |
| 5,320,609 | A | 6/1994 | Haber et al. | |
| 5,383,865 | A | 1/1995 | Michel | |
| 5,480,387 | A | 1/1996 | Gabriel et al. | |
| 5,505,704 | A | 4/1996 | Pawelka et al. | |
| 5,582,598 | A | 12/1996 | Chanoch | |
| 5,626,566 | A | 5/1997 | Petersen et al. | |
| 5,674,204 | A | 10/1997 | Chanoch | |
| 5,688,251 | A | 11/1997 | Chanoch | |
| 5,921,966 | A | 7/1999 | Bendek et al. | |
| 5,961,495 | A | 10/1999 | Walters et al. | |
| 6,004,297 | A | 12/1999 | Steenfeldt-Jensen et al. | |
| 6,193,698 | B1 | 2/2001 | Kirchhofer et al. | |
| 6,221,046 | B1 | 4/2001 | Burroughs et al. | |
| 6,235,004 | B1 | 5/2001 | Steenfeldt-Jensen et al. | |
| 6,248,095 | B1 | 6/2001 | Giambattista et al. | |
| 6,899,698 | B2 | 5/2005 | Sams | |
| 6,936,032 | B1 | 8/2005 | Bush, Jr. et al. | |
| 6,962,488 | B2 * | 11/2005 | Davis et al. | 417/477.2 |
| 7,241,278 | B2 | 7/2007 | Moller | |
| 8,496,621 | B2 * | 7/2013 | Basso et al. | 604/151 |
| 2002/0052578 | A1 | 5/2002 | Moller | |
| 2002/0120235 | A1 | 8/2002 | Enggaard | |
| 2003/0050609 | A1 | 3/2003 | Sams | |
| 2004/0059299 | A1 | 3/2004 | Moller | |
| 2004/0210199 | A1 | 10/2004 | Atterbury et al. | |
| 2004/0267207 | A1 | 12/2004 | Veasey et al. | |
| 2005/0113765 | A1 | 5/2005 | Veasey et al. | |
| 2006/0153693 | A1 | 7/2006 | Fiechter et al. | |
| 2006/0177329 | A1 | 8/2006 | Firmann | |
| 2009/0275916 | A1 | 11/2009 | Harms et al. | |

FOREIGN PATENT DOCUMENTS

| | | | |
|---|---|---|---|
| EP | 0937471 | A2 | 8/1999 |
| EP | 0937476 | A2 | 8/1999 |
| WO | 9938554 | A1 | 8/1999 |
| WO | 0110484 | A1 | 2/2001 |
| WO | 2007064927 | A2 | 6/2007 |
| WO | 2007085032 | A1 | 8/2007 |
| WO | 2008040477 | A1 | 4/2008 |
| WO | WO2008040477 | * | 4/2008 ............. F04B 43/12 |

* cited by examiner

PUMP CHAMBER FOR A PERISTALTIC PUMP

CROSS REFERENCE TO RELATED APPLICATIONS

The present application is a 35 U.S.C. 371 National Application of PCT/EP2010/060123 filed Jul. 14, 2010, which claims priority to European Patent Application No. 09009186.9 filed Jul. 14, 2009, the entire contents of which are incorporated entirely herein by reference.

The invention relates to a pump chamber for a peristaltic pump according to the preamble of claim 1.

Many medicaments have to be injected into the body. This applies in particular to medicaments, which are deactivated or have their efficiency remarkably decreased by oral administration, e.g. proteines (such as Insulin, growth hormones, interferons), carbohydrates (e.g. Heparin), antibodies and the majority of vaccines. Such medicaments are predominantly injected by means of syringes, medicament pens or medicament pumps.

A compact small scale peristaltic medicament pump is disclosed in DE 19 745 999. The pump comprises a delivery head, a drive unit for the delivery head, and speed control. The pump with the drive unit may be replaceably attached to a reusable backend in order to maintain a clean and sterile treatment by disposing the pump off and replacing it with a clean one after drug delivery.

WO 2008/040477 A1 discloses an injection arrangement with a peristaltic medicament pump, wherein the drive unit is integrated in the reusable backend rather than in the pump unit so the relatively expensive drive unit does not have to be disposed off every time the pump unit is replaced.

US2006/0177329 A1 discloses a pump chamber for a peristaltic pump, the pump chamber comprising an elongate cavity defined within an elastically deformable tube, wherein the tube is arranged at a rigid tube-bed, wherein the elastically deformable tube and the rigid tube-bed are arranged as a one-piece part by two-component injection moulding.

WO 2007/064927 A2 discloses a roller pump conduit defining a pump chamber. The roller pump conduit includes a roller contact portion having a fill region and a delivery region. The fill region has a first taper configured to determine volume delivery per revolution of a roller head. The delivery region has a pressure region having a second taper and a discharge region having a third taper. The third taper has a lesser degree of taper than the second taper. The delivery region is configured to produce a pulsatile flow out of the conduit. Furthermore, a roller, pump having a roller pump conduit is provided. The roller pump conduit of the roller pump has a fill region and a delivery region, the fill region having a first taper, and the delivery region having a second and third taper, wherein the third taper has lesser degree of taper than the second taper.

It is an object of the present invention to provide an improved pump chamber for a peristaltic pump and an improved method for producing such a pump chamber.

The object is achieved by a pump chamber according to claim 1 and by a method according to claim 18.

Preferred embodiments of the invention are given in the dependent claims.

According to the invention a pump chamber for a peristaltic pump comprises an elongate cavity defined between an elastically deformable chamber wall and a substantially rigid chamber wall. The elastically deformable wall and the rigid wall are arranged as a one-piece part by two-component injection moulding. Thus, only one process step is required for producing the pump chamber so costs for production and assembly may be reduced. Furthermore, the pump chamber according to the invention may be held in position more easily than the pump hoses known from conventional art peristaltic pumps.

Preferably the elastically deformable chamber wall has essentially the shape of a lengthwise split cylinder and the rigid chamber wall has an essentially planar shape at least in sections of the elongate cavity, so a pump rotor in a rotary design or a another squeezing tool in a linear pump design may press the elastically deformable chamber wall against the rigid chamber wall without leaving a considerable gap between the two parts.

In a rotary pump design the elongate cavity and thus the deformable and the rigid wall are at least partially arranged in a circular arc shape so as to allow the pump rotor of the peristaltic pump to engage a considerable length of the elastically deformable wall. However, 360° peristaltic pumps may also be designed with the elongate cavity having a 360° circular shape with open ends.

The pump chamber may be applied in a peristaltic pump, particularly for an injection arrangement for delivering a liquid medicament. In addition to the pump chamber, the peristaltic pump comprises a pump rotor having circumferential protrusions for engaging the elastically deformable wall of the pump chamber. The pump rotor may likewise be equipped with a different kind of roller, shoe or wiper circumferentially attached to the rotor for locally compressing the pump chamber. When the rotor is rotated the protrusions are advanced along the pump chamber thus advancing the squeezed portions of the deformable wall and the fluid (air or the liquid medicament) in the pump chamber ahead of the respective squeezed portion in rotational direction. Consequently, the fluid is forced out of an open end of the pump chamber. At the same time a vacuum is created behind the advancing squeezed portion thus intaking fluid from the other open end of the pump chamber.

An external side of the elastically deformable wall and/or the pump rotor or the protrusions may have an anti-stick coating, such as Teflon®. Thus dynamic friction between the pump hose and the pump rotor is reduced and consequently efficiency increased and abrasion reduced thus allowing for a longer service-life.

The peristaltic pump may be part of a pump unit for an injection arrangement for delivering a liquid medicament, the pump unit further comprising a medicament inlet and a medicament outlet, wherein the peristaltic pump serves for delivering the liquid medicament from the inlet to the outlet.

The medicament outlet may have a hollow needle attached for piercing a patients skin.

The essentially rigid chamber wall may be arranged as part of a housing of the pump unit. In this case the pump chamber could be produced by two-component moulding of the housing.

The pump unit may be replaceably attachable to a reusable backend of an injection arrangement for delivering a liquid medicament.

The pump rotor may have an adapter for engaging a drive shaft of a reusable backend. By integrating the drive unit in the reusable backend rather than in the disposable pump unit the relatively expensive drive unit does not have to be disposed off every time the pump unit is replaced.

The pump rotor may be designed as a one-part component with the protrusions being part of the rotor.

Preferably a flow sensor for determining a volume flow of the medicament is arranged in the pump unit and connectable to a control unit of a reusable backend thus allowing to control the volume of medicament to be delivered.

The pump unit and the reusable backend may be part of an injection arrangement for delivering a liquid medicament. The reusable backend may comprise a medicament container, a control unit, a drive unit and an energy source for powering the drive unit. The reusable backend may be used over the service-life of the entire injection arrangement while the pump unit may be replaced after each medicament delivery.

The pump unit may have easily disconnectable interfaces to the medicament container (ampoule), drive unit and control unit on the one hand and to the injection needle on the other hand.

The energy source for the drive unit may be a galvanic cell or battery of galvanic cells in case the drive unit comprises an electrical motor. Preferably the energy source is a rechargeable accumulator. The rechargeable accumulator may be replaceable or chargeable in place by an external charging device arranged for holding the reusable backend.

The rechargeable accumulator may be chargeable by an external charging device arranged for holding the reusable backend.

The reusable backend may further have a user interface for user interaction. This may comprise a dosing and/or trigger knob or wheel and/or a display, e.g for displaying a dose volume.

The pump chamber or the peristaltic pump or the pump unit or the reusable backend or the injection arrangement may preferably be used for delivering one of an analgetic, an anticoagulant, Insulin, an Insulin derivate, Heparin, Lovenox, a vaccine, a growth hormone, a peptide hormone, a proteine and complex carbohydrates.

Further scope of applicability of the present invention will become apparent from the detailed description given hereinafter. However, it should be understood that the detailed description and specific examples, while indicating preferred embodiments of the invention, are given by way of illustration only.

Figure 2:
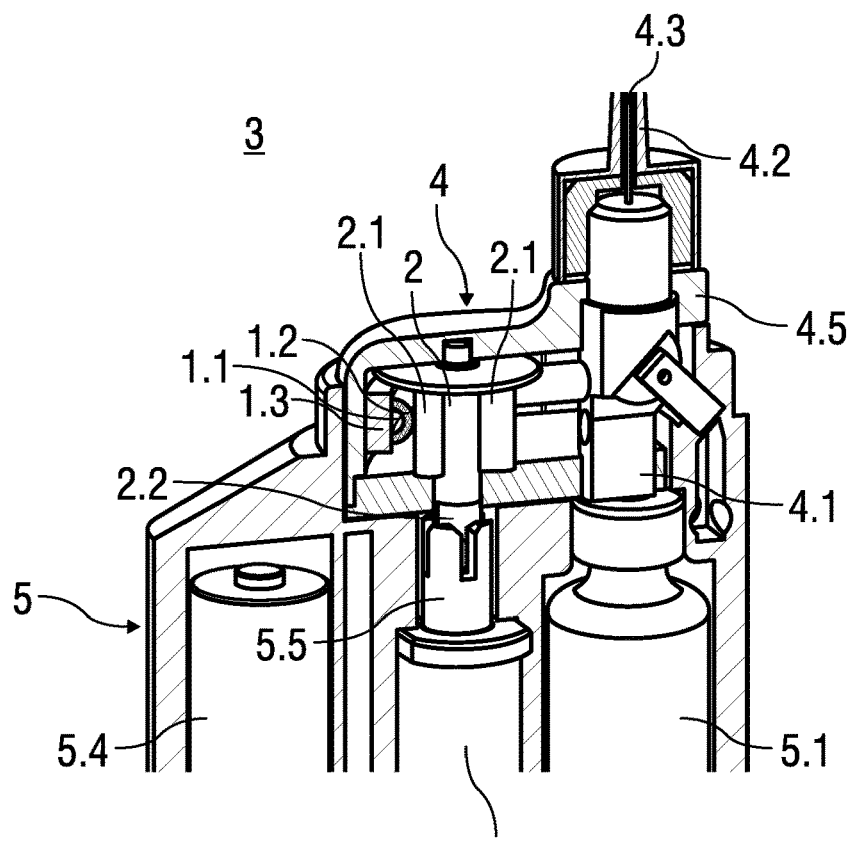
Figure 3:
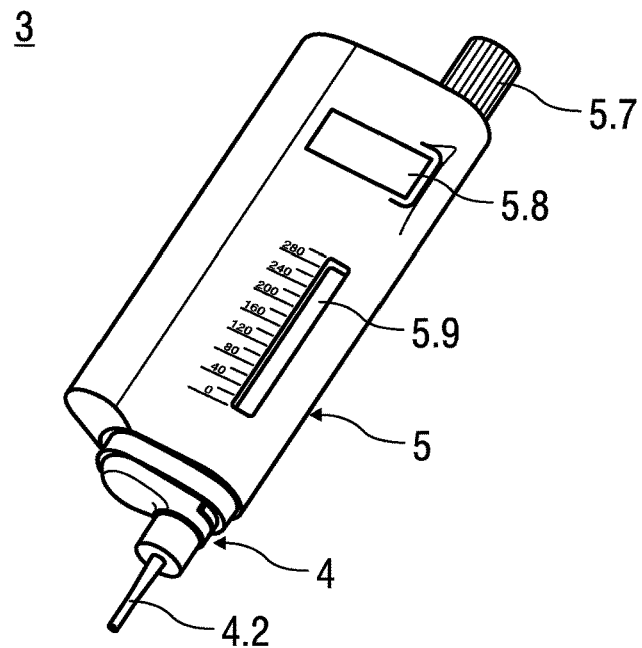
Figure 4:
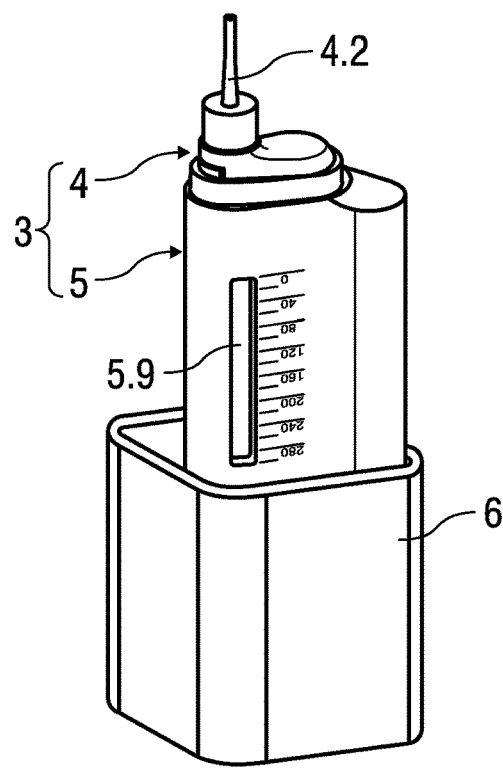
Figure 5:
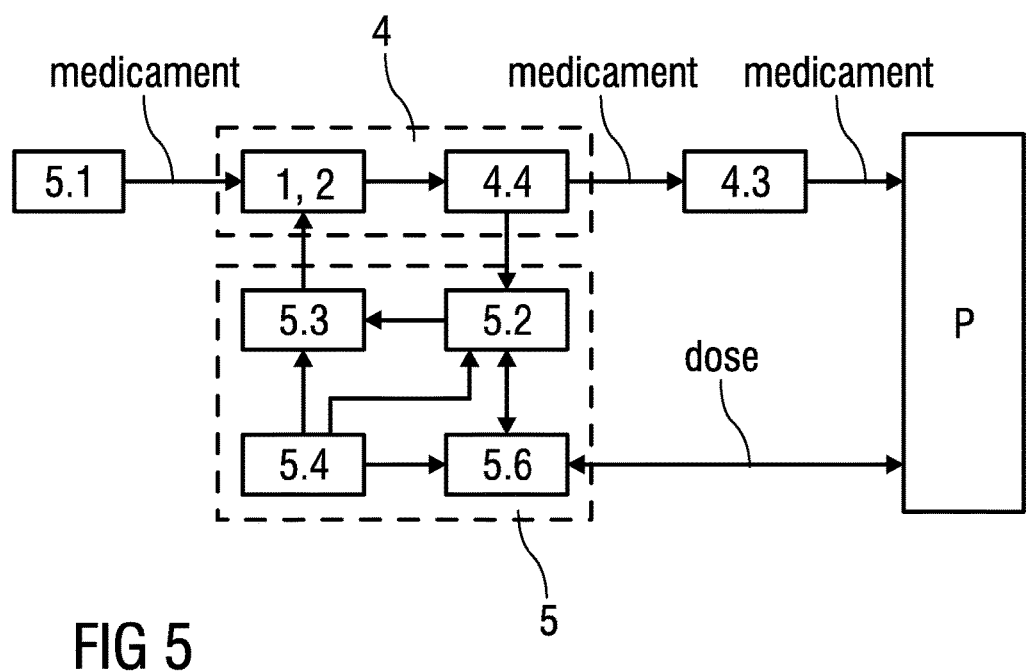

The present invention will become more fully understood from the detailed description given hereinbelow and the accompanying drawings which are given by way of illustration only, and thus, are not limitive of the present invention, and wherein:

FIG. 1 is a perspective view of a section of a pump chamber for a peristaltic pump, FIG. 2 is a perspective sectional view of an injection arrangement in an assembled state, FIG. 3 is a perspective view of the assembled injection arrangement, FIG. 4 is a perspective view of the injection arrangement held in a charger, and FIG. 5 is a schematic view of the injection arrangement.

Corresponding parts are marked with the same reference symbols in all figures.

FIG. 1 shows a perspective view of a section of a pump chamber 1 for a peristaltic pump.

The pump chamber 1 for a peristaltic pump comprises an elongate cavity 1.1 defined between an elastically deformable chamber wall 1.2 and an essentially rigid chamber wall 1.3. The elastically deformable wall 1.2 and the rigid chamber wall 1.3 are arranged as a one-piece part by two-component injection moulding.

The elastically deformable chamber wall 1.2 has essentially the shape of a lengthwise split cylinder. The rigid chamber wall 1.3 has an essentially planar shape at least in sections of the elongate cavity.

In a rotary pump design, such as shown in FIG. 2, the elongate cavity 1.1 and thus the deformable wall 1.2 and the rigid wall 1.3 are at least partially arranged in a circular arc shape so as to allow a pump rotor 2 of the peristaltic pump to engage a considerable length of the elastically deformable wall 1.2. However, 360° peristaltic pumps may also be designed with the elongate cavity 1.1 having a 360° circular shape with open ends.

FIG. 2 shows a perspective partial view of an injection arrangement 3 for delivering a liquid medicament with a replaceable pump unit 4 and a reusable backend 5.

The pump unit 4 is replaceably attachable to the reusable backend 5. The pump unit 4 comprises a medicament inlet 4.1, a medicament outlet 4.2 and the peristaltic pump for delivering the liquid medicament from the inlet 4.1 to the outlet 4.2. The peristaltic pump comprises the pump rotor 2 and the pump chamber 1. The pump chamber 1 is partially arranged around a perimeter of the pump rotor 2. The pump rotor 2 exhibits protrusions 2.1 for engaging the pump chamber 1. The protrusions 2.1 locally squeeze the elastically deformable chamber wall 1.2 against the essentially rigid chamber wall 1.3. When the rotor 2 is rotated the protrusions 2.1 are advanced along the pump chamber 1 thus advancing the squeezed portions of the pump chamber 1 and the fluid (air or the liquid medicament) in the pump chamber 1 ahead of the respective squeezed portion in rotational direction. Consequently, the fluid is forced out of the medicament outlet 4.2. At the same time a vacuum is created behind the advancing squeezed portion thus intaking fluid from the medicament inlet 4.1.

The reusable backend 5 comprises a replaceable medicament container 5.1, a control unit 5.2 shown in the schematic view in FIG. 5, a drive unit 5.3 and an energy source 5.4 for powering the drive unit 5.3.

The medicament container 5.1 may have a septum which is pierced by a backwardly pointing needle of the medicament inlet 4.1.

The medicament outlet 4.2 may have a hollow needle 4.3 attached for piercing a patients P skin. Alternatively, a jet nozzle may be provided.

The pump rotor 2 and/or the elastically deformable chamber wall 1.2 may have an anti-stick coating, such as Teflon®.

The pump rotor 2 has an adapter 2.2 for engaging a drive shaft 5.5 connected to the drive unit 5.3 of the reusable backend 5. The drive shaft 5.5 is preferably designed in a manner to ease this engagement (cf. FIGS. 1 and 2).

The pump rotor 2 is preferably designed as a one-part component with the protrusions 2.1 and the adapter 2.2 being part of the rotor 2.

The pump unit 4 further comprises a flow sensor 4.4 (shown in FIG. 7) for determining a flux or volume flow of the medicament. The flow sensor 4.4 is connectable to the control unit 5.2 thus allowing to control the volume of medicament to be delivered.

The pump unit 4 has easily disconnectable interfaces to the medicament container 5.1 (ampoule), the drive unit 5.3 and the control unit 5.2 on the one hand and to the hollow injection needle 4.3 on the other hand, e.g. by Luer-Lok® or Luer-Slip®.

The energy source 5.4 may be a galvanic cell or battery of galvanic cells in case the drive unit 5.3 comprises an electrical motor. Preferably, the energy source 5.4 is a rechargeable accumulator. The rechargeable accumulator may be replaceable or chargeable in place by an external charging device 6 arranged for holding the reusable backend 5 (see FIG. 4).

The reusable backend 5 may further have a user interface 5.6 for user interaction. This may comprise a dosing and/or trigger knob 5.7 or wheel and/or a display 5.8, e.g for displaying a dose volume.

The reusable backend 5 may further comprise a viewing window 5.9 for inspecting the contents of the medicament container 5.1.

The pump chamber 1 or the peristaltic pump or the pump unit 4 or the reusable backend 4 or the injection arrangement 3 may preferably be used for delivering one of an analgetic, an anticoagulant, Insulin, an Insulin derivate, Heparin, Lovenox, a vaccine, a growth hormone and a peptide hormone.

For performing an injection a user sets a required target dose at the user interface 5.6. The required target dose is forwarded to the control unit 5.2 and stored there. As soon as the user triggers the injection arrangement, e.g by pressing the knob 5.7, the target dose is converted into a flow sensor setpoint and the drive unit 5.3 is started. The drive unit 5.3 converts the electrical energy provided by the energy source 5.4 into mechanical energy and forwards it to the peristaltic pump. There the energy is again converted into fluidic energy causing a volume flow of the medicament. The integrated flow sensor 4.4 acquires the volume flow and forwards measurement values to the control unit 5.2. The measurement values, particularly when in the shape of increments corresponding to volume increments may be integrated by the control unit 5.2 and the drive unit 5.3 switched off upon delivery of the setpoint volume. After delivery the control unit 5.2 may generate a message for the user to be displayed by the display unit 5.8.

The essentially rigid chamber wall 1.3 may be arranged separately as shown in FIG. 1 or as part of a housing 4.5 of the pump unit 4. In this case the pump chamber 1 may be produced by two-component moulding of the housing 4.5.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4 (1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

LIST OF REFERENCES 1 pump chamber
elongate cavity
elastically deformable chamber wall
essentially rigid chamber wall
2 pump rotor
protrusion
adapter
3 injection arrangement
4 pump unit
medicament inlet
medicament outlet
hollow needle
flow sensor
housing
5 reusable backend
medicament container
control unit
drive unit
energy source
drive shaft
user interface
dosing/trigger knob
display
viewing window
6 external charging device
P patient

The invention claimed is:

1. A pump chamber for a peristaltic pump for pumping a fluid, the pump chamber comprising an elongate cavity defined between an elastically deformable chamber wall and a rigid chamber wall, the elongate cavity configured to permit the fluid to pass therethrough, the elastically deformable chamber wall defining a width of the elongate cavity,
wherein the elastically deformable chamber wall and the rigid chamber wall are arranged as a one-piece part by two-component injection moulding,
wherein the elastically deformable chamber wall has the shape of a lengthwise split hollow cylinder when in an undeformed state,
wherein, in a first section along a length of the elongate cavity, the rigid chamber wall has a planar shape, and
wherein the pump chamber is configured to be at least partially arranged around a perimeter of a rotor of the peristaltic pump, with the rigid chamber wall being arranged in a circular arc shape in a second section along the length of the elongate cavity such that a portion of the rigid chamber wall extending between the elastically deformable chamber wall is curved in the circular arc shape in the second section along the length of the elongate cavity.

2. The pump chamber according to claim 1, wherein the circular arc shape of the second section of the rigid chamber wall allows the rotor of the peristaltic pump to engage a portion of a length of the elastically deformable chamber wall.

3. The pump chamber according to claim 1, wherein an external side of the elastically deformable chamber wall comprises an anti-stick coating.

4. A peristaltic pump for an injection arrangement for delivering a liquid medicament, the peristaltic pump comprising the pump chamber according to claim 1 and a rotor, wherein the rotor comprises circumferential protrusions for engaging the elastically deformable chamber wall of the pump chamber, wherein the circumferential protrusions of the rotor and the pump chamber are configured such that rotation of the rotor and corresponding advancement of the circumferential protrusions in an azimuthal direction cause one or more of the circumferential protrusions in contact with the pump chamber to squeeze the elastically deformable chamber wall against the rigid chamber wall, and to advance the corresponding one or more squeezed portions of the elastically deformable chamber wall and the fluid in the pump chamber ahead of each respective squeezed portion in an azimuthal direction, thereby forcing the fluid in the pump chamber ahead of each respective squeezed portion out of an open end of the pump chamber.

5. The peristaltic pump according to claim 4, wherein the rotor further comprises an anti-stick coating or the circumferential protrusions further comprise an anti-stick coating.

6. A pump unit for an injection arrangement for delivering a fluid in form of a liquid medicament, the pump unit comprising a medicament inlet, a medicament outlet, and the peristaltic pump according to claim 4 for delivering the liquid medicament from the medicament inlet to the medicament outlet.

7. The pump unit according to claim 6, wherein the rigid chamber wall is part of a housing of the pump unit.

8. The pump unit according to claim 6, wherein the rotor further comprises an adapter for engaging a drive shaft of a reusable backend.

9. The pump unit according to claim 6, wherein the rotor is a one-piece component.

10. The pump unit according to claim 6, further comprising a flow sensor for determining a volume flow of the liquid medicament, the flow sensor being arranged in the pump unit and connectable to a control unit of a reusable backend.

11. An injection arrangement for delivering a liquid medicament, the injection arrangement comprising a reusable backend and the pump unit according to claim 6, wherein the pump unit is replaceably attachable to the reusable backend, and wherein the reusable backend comprises a medicament container, a control unit, a drive unit, and an energy source for powering the drive unit.

12. The injection arrangement according to claim 11, wherein the control unit is connectable to a flow sensor for determining a volume flow of the liquid medicament, and wherein the flow sensor is arranged in the pump unit.

13. The injection arrangement according to claim 11, wherein the energy source is a rechargeable accumulator.

14. The injection arrangement according to claim 11, wherein the rechargeable accumulator is chargeable by an external charging device arranged for holding the reusable backend.

15. The injection arrangement according to claim 11, wherein a user interface for user interaction is arranged in the reusable backend.

16. The pump unit according to claim 6, wherein the pump unit is replaceably attachable to a reusable backend of the injection arrangement for delivering the liquid medicament.

17. The pump chamber according to claim 1, wherein the first section along the length of the elongate cavity is longer than the width of the elongate cavity.

18. A pump chamber for a peristaltic pump for pumping a fluid, the pump chamber comprising an elongate cavity defined between an elastically deformable chamber wall and a rigid chamber wall, the elongate cavity configured to permit the fluid to pass therethrough, the elongate cavity connecting an inlet and an outlet,
  wherein the elastically deformable chamber wall and the rigid chamber wall are arranged as a one piece part by two-component injection moulding,
  wherein the elastically deformable chamber wall has the shape of a lengthwise split hollow cylinder when in an undeformed state,
  wherein the rigid chamber wall has a planar shape in a first section along a length of the elongate cavity and is configured to be arranged in a circular arc shape in a second section along the length of the elongate cavity such that a portion of the rigid chamber wall extending between the elastically deformable chamber wall is curved in the circular arc shape in the second section along the length of the elongate cavity, and
  wherein the first section along the length of the elongate cavity is between the second section along the length of the elongate cavity and the outlet.

19. A pump chamber for a peristaltic pump for pumping a fluid, the pump chamber comprising an elongate cavity defined between an elastically deformable chamber wall and a rigid chamber wall, the elongate cavity configured to permit the fluid to pass therethrough, the elastically deformable chamber wall defining a width of the elongate cavity and the elongate cavity having a 360 degree circular shape with open ends,
  wherein the elastically deformable chamber wall and the rigid chamber wall are arranged as a one-piece part by two-component injection moulding,
  wherein the elastically deformable chamber wall has the shape of a lengthwise split hollow cylinder when in an undeformed state,
  wherein at least in one or more sections spanning the width of the elongate cavity, the rigid chamber wall has a planar shape, and
  wherein the pump chamber is configured to be at least partially arranged around a perimeter of a rotor of the peristaltic pump, with the rigid chamber wall being arranged in a circular arc shape along at least part of a length of the elongate cavity.

* * * * *